United States Patent
McLoughlin

(10) Patent No.: US 12,343,498 B2
(45) Date of Patent: Jul. 1, 2025

(54) SYSTEM FOR VERIFYING ACCURACY OF SERIALLY-CONNECTED DRUG MODULES IN A COMBINATORIAL DRUG DELIVERY DEVICE

(71) Applicant: Bristol-Myers Squibb Company, Princeton, NJ (US)

(72) Inventor: Martin John McLoughlin, Hillsborough, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 0 days.

(21) Appl. No.: 18/386,398

(22) Filed: Nov. 2, 2023

(65) Prior Publication Data

US 2024/0058529 A1     Feb. 22, 2024

Related U.S. Application Data

(63) Continuation of application No. 17/770,682, filed as application No. PCT/US2020/056660 on Oct. 21, 2020, now Pat. No. 11,844,927.

(Continued)

(51) Int. Cl.
    *A61M 5/145*     (2006.01)
    *A61M 5/168*     (2006.01)

(52) U.S. Cl.
    CPC ........ *A61M 5/145* (2013.01); *A61M 5/16804* (2013.01); *A61M 2205/3553* (2013.01)

(58) Field of Classification Search
    CPC .............. A61M 5/145; A61M 5/16804; A61M 2205/3553; A61M 2205/3561;

(Continued)

(56) References Cited

U.S. PATENT DOCUMENTS

| | | | |
|---|---|---|---|
| 9,539,178 B1 * | 1/2017 | Valerino, Sr. | B65G 43/08 |
| 10,002,277 B1 * | 6/2018 | Endress | G06K 7/1417 |

(Continued)

FOREIGN PATENT DOCUMENTS

| | | |
|---|---|---|
| CA | 2655490 A1 | 1/2008 |
| CA | 2712626 A1 | 8/2009 |

(Continued)

OTHER PUBLICATIONS

International Search Report and Written Opinion of the International Searching Authority from PCT International Application No. PCT/US2020/056660, dated Jan. 12, 2021.

(Continued)

*Primary Examiner* — Tuyen K Vo
(74) *Attorney, Agent, or Firm* — Budzyn IP Law, LLC

(57) ABSTRACT

In one aspect, a system is provided of verifying the accuracy of a plurality of serially-connected drug modules of a combinatorial drug delivery device, each of the drug modules including a drug reservoir, the system including: a machine-readable code located on each of the drug modules; application software configured to generate an activation code based on the machine-readable codes and the sequence of the machine-readable codes; a flow controller on the drug delivery device which is selectively actuatable to a use state to permit flow of drug from the drug delivery device; and, a control unit on the drug delivery device having a computing processing unit configured to compare the activation code with an authentication code, and, wherein, if the authentication code matches the activation code, the computing processing unit causes actuation of the flow controller to permit flow of the drug from the drug delivery device.

19 Claims, 10 Drawing Sheets

Related U.S. Application Data

(60) Provisional application No. 62/932,825, filed on Nov. 8, 2019.

(58) Field of Classification Search
CPC .... A61M 2205/3584; A61M 2205/505; A61M 2205/6018; A61M 2205/6072; A61M 5/1409; A61M 5/16827; G16H 20/17; G16H 40/63; G16H 40/67; G16H 70/40; G16H 20/13
See application file for complete search history.

(56) References Cited

U.S. PATENT DOCUMENTS

| | | | |
|---|---|---|---|
| 11,701,483 | B2 | 7/2023 | Smith |
| 11,705,236 | B2 | 7/2023 | Chudy et al. |
| 2004/0167804 | A1 | 8/2004 | Simpson et al. |
| 2006/0206356 | A1 | 9/2006 | Vanderveen |
| 2007/0068959 | A1* | 3/2007 | D'Silva .................. G07F 9/02 221/7 |
| 2011/0125523 | A1* | 5/2011 | Tanimoto ............. G16H 40/20 705/2 |
| 2014/0248159 | A1 | 9/2014 | Marsh et al. |
| 2015/0025464 | A1 | 1/2015 | McTaggart et al. |
| 2017/0287290 | A1* | 10/2017 | Nelson .................. G01N 21/65 |
| 2018/0177682 | A1* | 6/2018 | Tanaka ................. A61J 7/0084 |
| 2019/0001057 | A1 | 1/2019 | Tsoukalis |
| 2019/0279763 | A1* | 9/2019 | Tsai .................... G06K 19/0701 |
| 2019/0279764 | A1* | 9/2019 | Tsai .................... G06K 7/1413 |
| 2020/0105393 | A1* | 4/2020 | Keefe .................. A61M 5/315 |
| 2022/0001103 | A1* | 1/2022 | Jense .................. A61M 39/10 |

FOREIGN PATENT DOCUMENTS

| | | |
|---|---|---|
| CA | 2723444 A1 | 10/2009 |
| CA | 2934359 A1 | 8/2015 |
| CA | 3094888 A1 | 11/2018 |
| CN | 101438327 A | 5/2009 |
| CN | 105025952 A | 11/2015 |
| WO | 2007107406 A2 | 9/2007 |
| WO | 2007126851 A2 | 11/2007 |
| WO | 2012020086 A2 | 2/2012 |
| WO | 2023173015 A1 | 11/2013 |
| WO | 2017181287 A1 | 10/2017 |
| WO | 2019217820 A1 | 11/2019 |
| WO | 2019217845 A1 | 11/2019 |
| WO | 2019217864 A1 | 11/2019 |

OTHER PUBLICATIONS

Extended European Search Report for European Application No. 20885257.4 dated Nov. 17, 2022.

Office Action from Chinese Patent Application No. 202080077991.7 issued on Jun. 22, 2023.

* cited by examiner

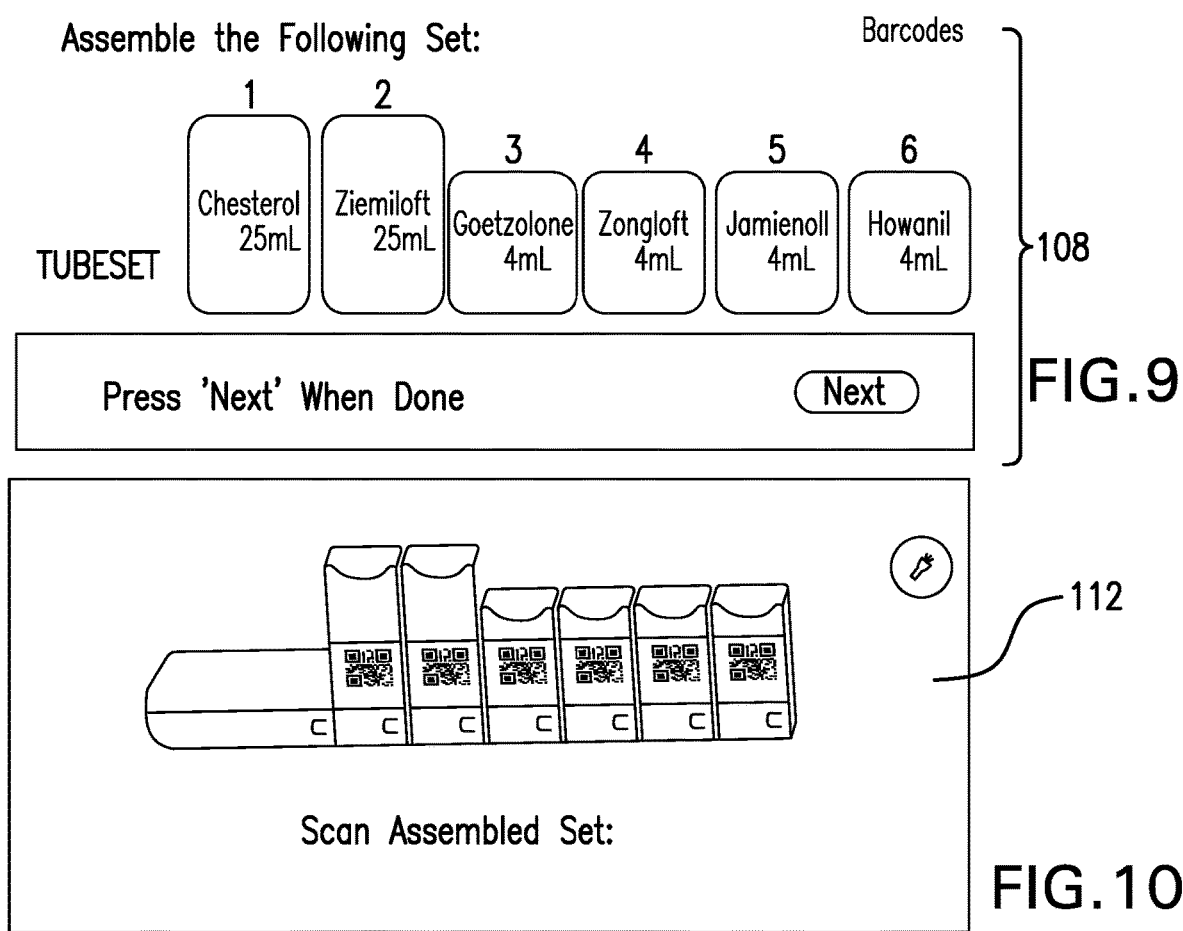
FIG. 9
FIG. 10
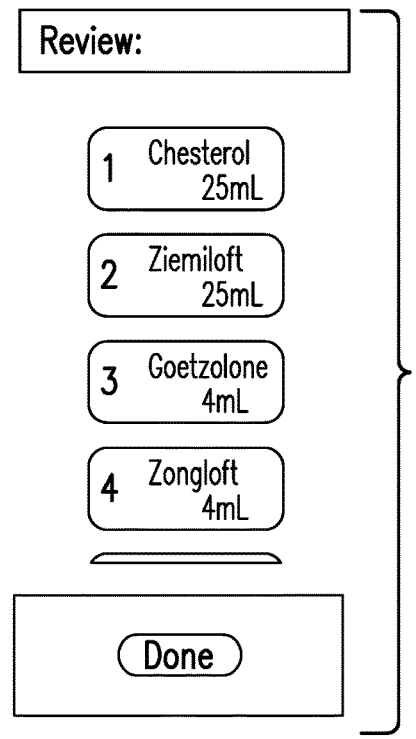
FIG. 11

SYSTEM FOR VERIFYING ACCURACY OF SERIALLY-CONNECTED DRUG MODULES IN A COMBINATORIAL DRUG DELIVERY DEVICE

CROSS-REFERENCE TO RELATED APPLICATIONS

This application is a continuation of U.S. application Ser. No. 17/770,682, filed Apr. 21, 2022, now allowed, which is a National Stage Application under 35 U.S.C. § 371 of PCT Application No. PCT/US2020/056660, filed Oct. 21, 2020, which claims the priority benefit of U.S. Provisional Application No. 62/932,825, filed Nov. 8, 2019; the contents of which are herein incorporated by reference in their entireties.

BACKGROUND OF THE INVENTION

Combinatorial drug delivery devices and systems are shown and described in: U.S. Provisional Patent Appl. No. 62/670,266, filed May 11, 2018; PCT Appl. No. PCT/US2019/031727, filed May 10, 2019; PCT Appl. No. PCT/US2019/031762, filed May 10, 2019; and, PCT Appl. No. PCT/US2019/031791, filed May 10, 2019. All of the aforementioned patent filings are by the same assignee as herein. As shown in the aforementioned patent filings, drug modules of different liquid drugs may be provided in various combinations to provide different (individualized) drug combinations. The drug modules may be nested, i.e., connected, in series or in parallel, on a tray or other base structure. Alternatively, the drug modules may be serially connected (vertically and/or horizontally) directly to one another. U.S. Provisional Patent Appl. No. 62/670,266, PCT Appl. No. PCT/US2019/031727, PCT Appl. No. PCT/US2019/031762, and, PCT Appl. No. PCT/US2019/031791, are incorporated by reference herein in their respective entireties.

The serially-connected combinatorial system has the advantage in comparison with the nested designs in that it does not require a separate tray component to make the fluid connections and is therefore more efficient in components and, thus, in supply chain.

In the nested system, the tray design can 'store' information on the correct configuration of the modules through the inherent design and layout of the tray design. For example, the tray may provide a configuration (e.g., mechanical cooperating features, such as "lock and key" features) that guarantee only the correct drug modules can be inserted into the nests of the tray and that the correct drug modules are arranged in the correct order. This acts as a safety check in preparing the drug modules for use. In contrast, the serially-connected system does not have a tray-type element and, thus, lacks the ability to have a safety check on this basis.

Because tray-based mechanical means of error prevention are not possible in the serially-connected case, it is desirable to implement other means of detecting configuration errors in the serially-connected system and hence prevent the occurrence of medication errors.

SUMMARY OF THE INVENTION

In one aspect, the subject invention provides a system of verifying the accuracy of a plurality of serially-connected drug modules of a combinatorial drug delivery device, each of the drug modules including a drug reservoir for accommodating a liquid drug, the system including: a machine-readable code located on each of the drug modules; application software on a user's mobile device, the application software configured to read the machine-readable codes in a captured digital image of the serially-connected drug modules, the application software configured to generate an activation code based on the machine-readable codes and the sequence of the machine-readable codes; a transmitter on the user's mobile device configured to transmit the activation code; a flow controller on the drug delivery device, the flow controller being selectively actuatable to a use state to permit flow of the liquid drug from the drug delivery device; and, a control unit on the drug delivery device having a computing processing unit and a receiver, the computing processing unit having an associated memory with an authentication code stored thereon, wherein, the receiver is configured to receive the activation code transmitted by the transmitter, wherein, the computing processing unit is configured to compare the activation code with the authentication code, and, wherein, if the authentication code matches the activation code, the computing processing unit is configured to cause actuation of the flow controller to the use state to permit flow of the liquid drug from the drug delivery device.

In a further aspect, the subject invention provides a system of verifying the accuracy of a plurality of serially-connected drug modules of a combinatorial drug delivery device, each of the drug modules including a drug reservoir for accommodating a liquid drug, the system including: a machine-readable code located on each of the drug modules; application software on a user's mobile device, the application software configured to read the machine-readable codes in a captured digital image of the serially-connected drug modules, the application software configured to generate an activation code based on the machine-readable codes and the sequence of the machine-readable codes, wherein the application software includes an application programming interface to call a remote server to obtain an authentication code associated with the drug delivery device, the application software configured to compare the activation code and the authentication code, wherein, if there is a match between the authentication code and the activation code, the application software generating an approval message; a transmitter on the user's mobile device configured to transmit the approval message; a flow controller on the drug delivery device, the flow controller being selectively actuatable to a use state to permit flow of the liquid drug from the drug delivery device; and, a control unit on the drug delivery device having a computing processing unit and a receiver, wherein, the receiver is configured to receive the approval message transmitted by the transmitter, and, wherein, based upon the approval message, the computing processing unit is configured to cause actuation of the flow controller to the use state to permit flow of the liquid drug from the drug delivery device.

In a further aspect, the subject invention provides a system of verifying the accuracy of a plurality of serially-connected drug modules of a combinatorial drug delivery device, each of the drug modules including a drug reservoir for accommodating a liquid drug, the system including: a drug module machine-readable code located on each of the drug modules; application software on a user's mobile device, the application software configured to read the drug module machine-readable codes in a captured digital image of the serially-connected drug modules and to read a secondary machine-readable code representing an authentication code, the application software configured to generate an activation code based on the drug module machine-readable codes and the sequence of the drug module machine-readable codes, wherein the application software configured to compare the activation code and the authentication code, wherein, if there is a match between the authentication code and the activation code, the application software generating an approval message; a transmitter on the user's mobile device configured to transmit the approval message; a flow controller on the drug delivery device, the flow controller being selectively actuatable to a use state to permit flow of the liquid drug from the drug delivery device; and, a control unit on the drug delivery device having a computing processing unit and a receiver, wherein, the receiver is configured to receive the approval message transmitted by the transmitter, and, wherein, based upon the approval message, the computing processing unit is configured to cause actuation of the flow controller to the use state to permit flow of the liquid drug from the drug delivery device.

In yet a further aspect, the subject invention provides a system of verifying the accuracy of a plurality of serially-connected drug modules of a combinatorial drug delivery device, each of the drug modules including a drug reservoir for accommodating a liquid drug, the system including: a machine-readable code located on each of the drug modules; application software on a user's mobile device, the application software configured to read the machine-readable codes in a captured digital image of the serially-connected drug modules, the application software configured to generate an activation code based on the machine-readable codes and the sequence of the machine-readable codes; a transmitter on the user's mobile device configured to transmit the activation code; a remote server having stored thereon an authentication code associated with the drug delivery device, the remote server configured to receive the activation code transmitted by the transmitter, wherein, the remote server being configured to compare the activation code and the authentication code, wherein, if the authentication code matches the activation code, the remote server being configured to generate an approval message and to transmit the approval message, wherein, upon receipt of the approval message, the transmitter on the user's mobile device transmits the approval message; a flow controller on the drug delivery device, the flow controller being selectively actuatable to a use state to permit flow of the liquid drug from the drug delivery device; and, a control unit on the drug delivery device having a computing processing unit and a receiver, wherein, the receiver is configured to receive the approval message transmitted by the transmitter on the user's mobile device, and, wherein, based upon the approval message, the computing processing unit is configured to cause actuation of the flow controller to the use state to permit flow of the liquid drug from the drug delivery device.

These and other features of the invention will be better understood through a study of the detailed description and accompanying drawings.

BRIEF DESCRIPTION OF THE DRAWINGS

FIGS. 1-15 depict various features of a system formed in accordance with the subject invention.

DETAILED DESCRIPTION OF THE INVENTION

Figure 1:
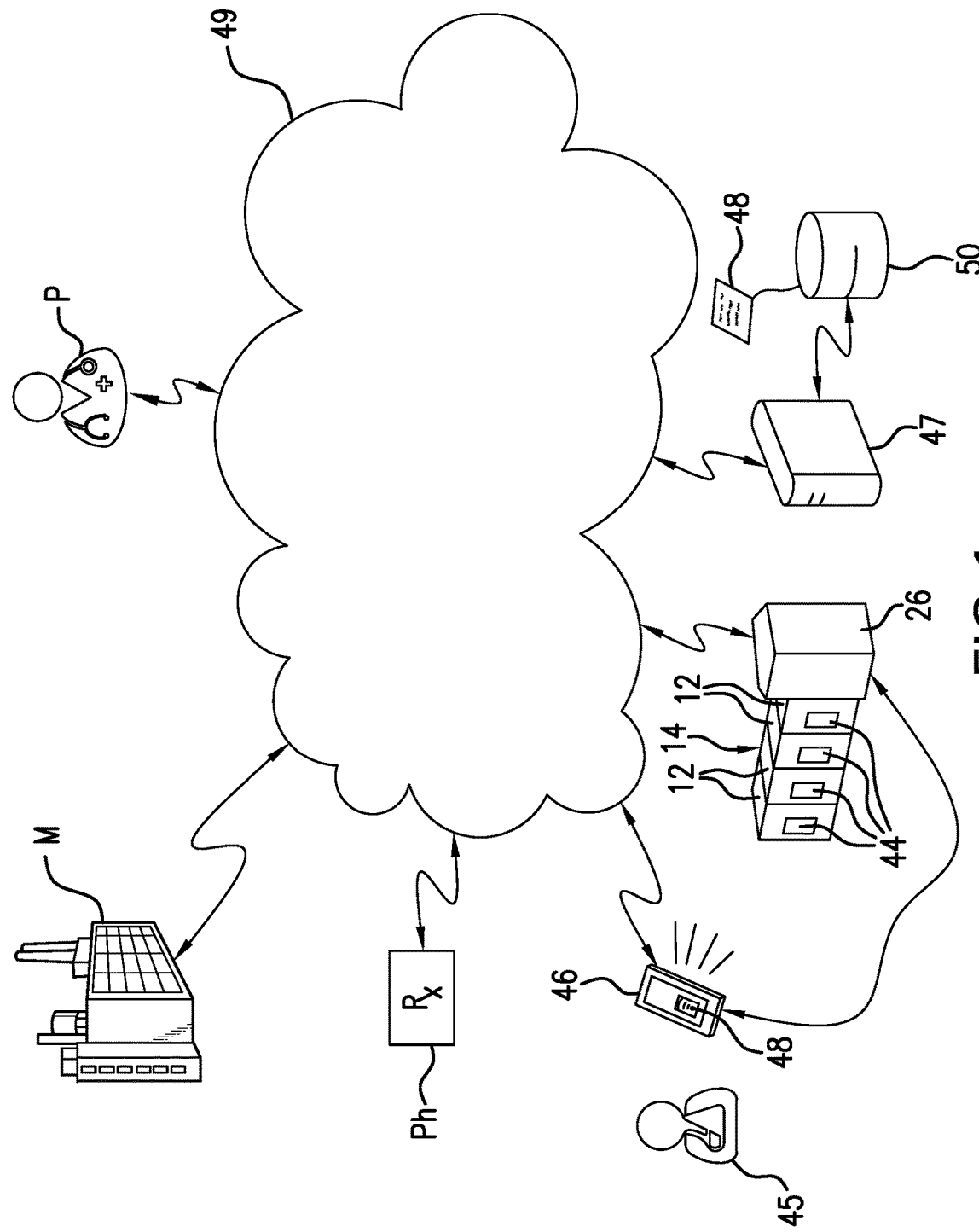

With reference to FIG. 1, a system 10 is shown useable to verify the accuracy of a plurality of serially-connected drug modules 12 of a combinatorial drug delivery device 14. Each of the drug modules 12 includes a drug reservoir 16 for accommodating a liquid drug 18. The drug reservoirs 16 may be defined by portions of the drug modules 12, or be defined by components, such as vials, inserted into the drug modules 12. The combinatorial drug delivery device 14, including any aspect thereof, may be formed in accordance with any of the embodiments disclosed in any of U.S. Provisional Patent Appl. No. 62/670,266, PCT Appl. No. PCT/US2019/031727, PCT Appl. No. PCT/US2019/031762, and, PCT Appl. No. PCT/US2019/031791. For illustrative purposes, exemplary features of the combinatorial drug delivery device 14 are described herein. As will be recognized by those skilled in the art, the subject invention is useable with any of the combinatorial drug delivery devices, including being useable with any of the elements thereof (e.g., system 10, drug modules 12, manner of connecting the drug modules 12, flow controller 34, etc.), disclosed in any of the aforementioned patent filings.

Figure 2:
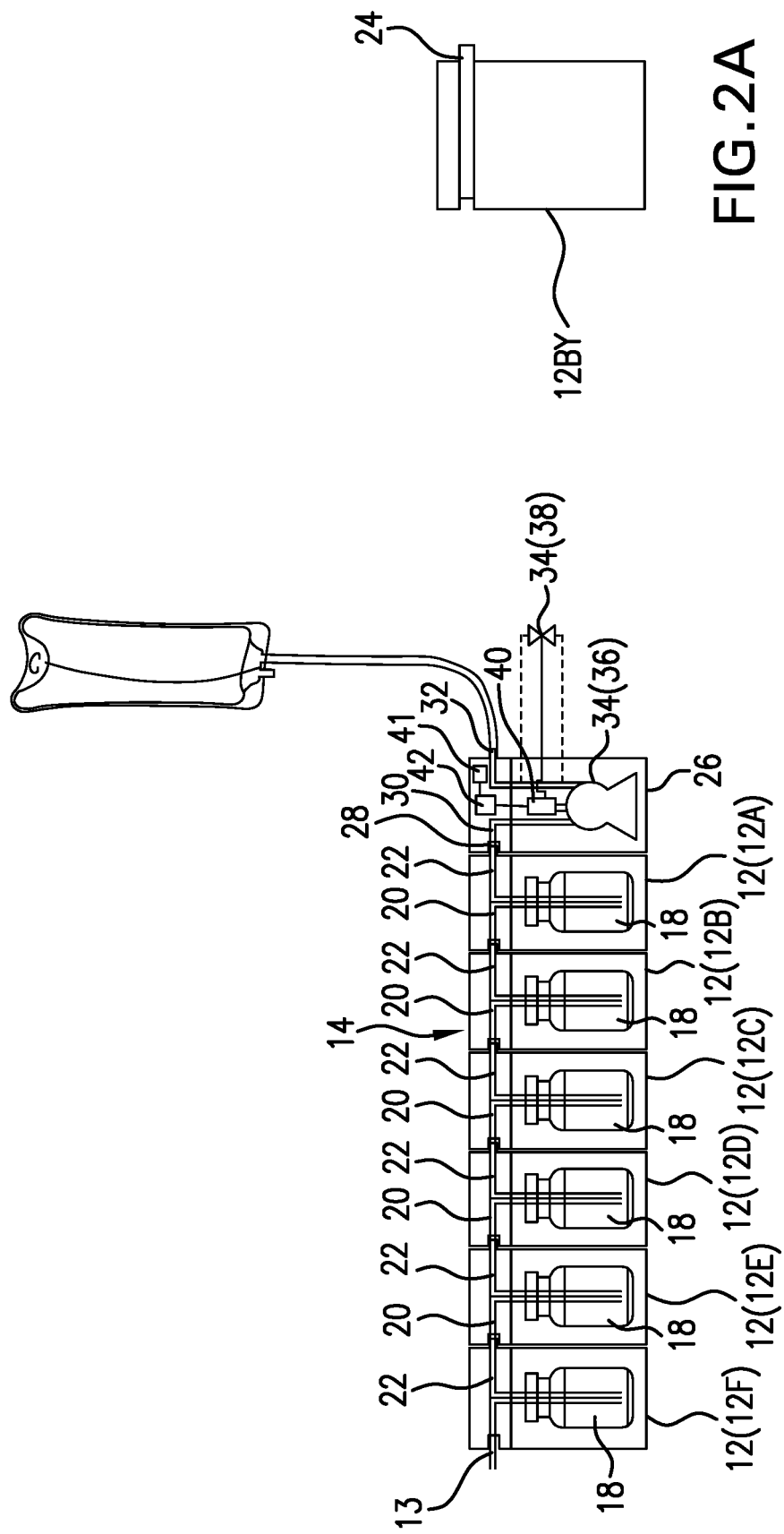
Figure 3:
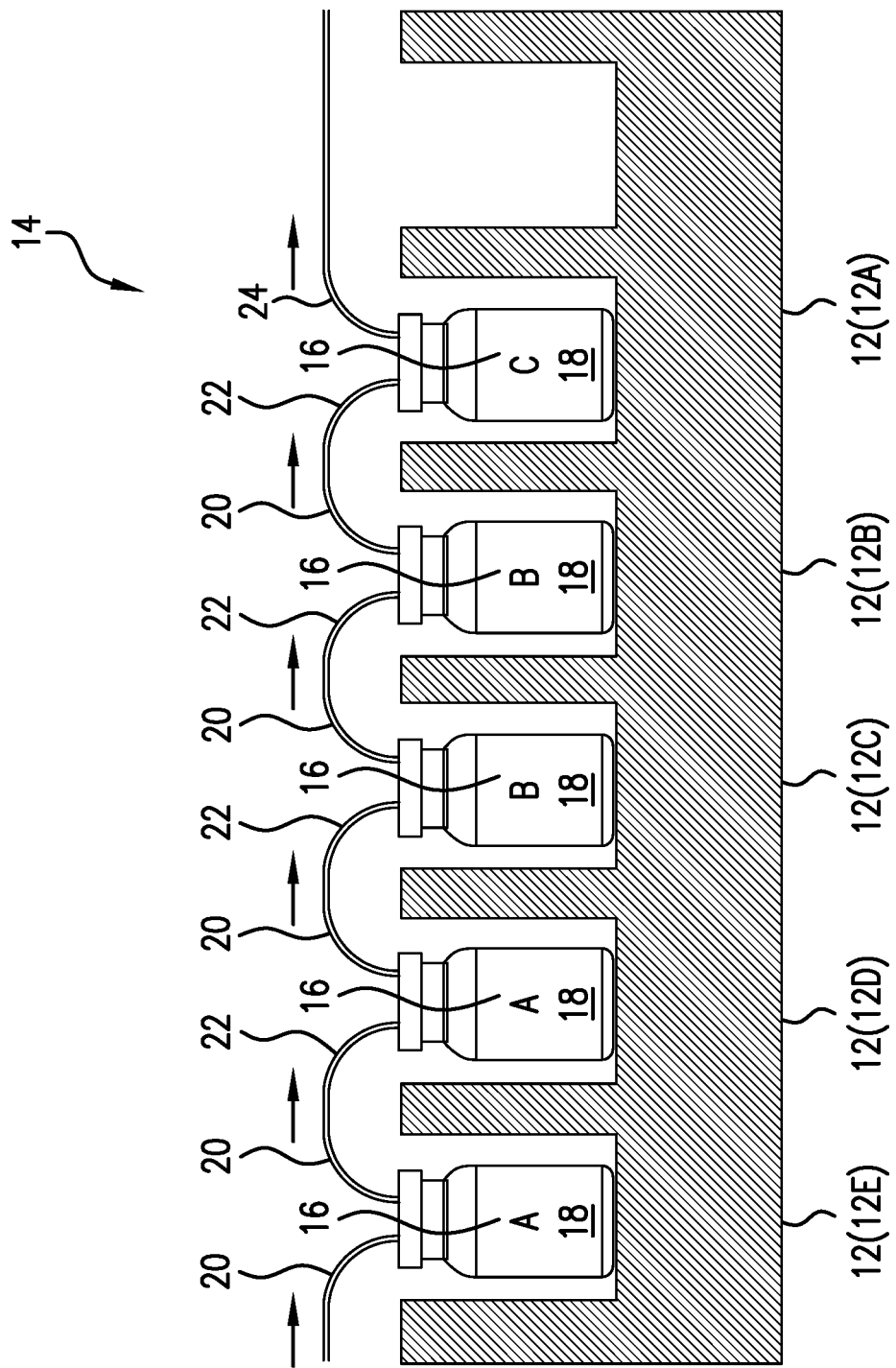

As shown in FIG. 2, the drug modules 12 are serially-connected so as to define a single flow path for the drug delivery device 14 through the series of the drug modules 12, through which the liquid drug 18 of each of the drug modules 12 may be drawn. As shown in FIG. 2, inlet and outlet tubing 20, 22, may be provided for each of the drug modules 12 so that the liquid drug 18 may be drawn, in succession, from each of the drug modules 12. As shown in FIG. 3, the inlet and outlet tubing 20, 22 may be formed continuously between the drug reservoirs 16 so that lengths of tubing are provided serving both as an outlet of one of the drug reservoirs 16 and an inlet for the next drug reservoir 16. FIG. 2 shows six of the drug modules 12 (12A-12F). As will be appreciated by those skilled in the art, any quantity of the drug modules 12 may be utilized. A vent 13 may be provided at a terminus of the flow path (in the ultimate drug module).

It is noted that one or more by-pass drug modules 12BY may be needed in a series, to accommodate a place in the series, but to not contain any liquid drug. As shown in FIG. 2A, the by-pass drug module 12BY may have by-pass tubing 24 which extends from the inlet to the outlet thereof to allow for flow therethrough without a drug reservoir. Alternatively, as shown in FIG. 3, the by-pass tubing 24 may be provided in lieu of one of the drug modules 12 to connect two components of the drug delivery device 14, such as two of the drug modules 12 or one of the drug modules 12 and the controller housing described below.

The liquid drugs 18 contained in the drug modules 12 may vary in type and concentration. The liquid drug 18 in some of the modules 12 may be a diluent with no pharmaceutically or biologically active agents. The drug modules 12 may contain one or more solid components which can be reconstituted with flow of a diluent therein to form a liquid drug. The ability of the serially-connected drug modules 12 to contain various drug types and concentrations allows for the drug delivery device 14 to be a combinatorial drug delivery device 14, providing for the mixing of various liquid drugs. The liquid drugs 18 intended for a particular combination for a patient is prescribed by a physician. The subject invention provides for the confirmation of accuracy of the inclusion of the particular drug modules 12 in the drug delivery device 14, as well as, the sequence of the drug modules 12. The sequence of the drug modules 14 may be significant, possibly having an impact on the efficacy of the ultimate resulting combination.

The drug delivery device 14 preferably includes a controller housing 26 to which the serially-connected drug modules 12 are connected. The outlet tubing 22 of the first drug module 12A (being the closest to the controller housing 26) is in communication with an inlet 28 formed in the controller housing 26 into which the liquid drug 18 may flow from the drug modules 12. Delivery tubing 30 extends from the inlet 28 to convey the liquid drug 18 through the controller housing 26 to an outlet 32. Tubing or conveyances may be secured to the outlet 32 to direct the liquid drug 18 to a storage device (e.g., an IV bag, injector) or to a drug delivery device connected to a patient (e.g., a butterfly needle).

A flow controller 34 is provided in the controller housing 26 which selectively regulates flow through the delivery tubing 30. In one embodiment, the flow controller 34 may include an actuatable source of negative pressure 36, such as a pump, provided in the controller housing 26 to draw the liquid drug 18 through the inlet 28 and discharge the liquid drug 18 through the outlet 32, via the delivery tubing 30 (which may be discontinuous). In a quiescent state, the source of negative pressure 36 generates no negative pressure, thus, not drawing the liquid drug 18. In a further embodiment, the flow controller 34 may include one or more adjustable valves 38 provided in the controller housing 26 configured to selectively regulate flow through the delivery tubing 30, particularly being configured to be selectively adjusted between open and closed states, such as a ball valve. With the use of the valves 38, a source of negative pressure external to the controller housing 26 may be utilized which is configured to apply negative pressure to the outlet 32 to draw the liquid drug 18 therefrom.

A control unit 40 may be provided in the controller housing 26 which includes a computing processing unit (CPU) 42. It is preferred that the flow controller 34 be electrically powered to be controlled by the CPU 42. For example, an electrical motor or actuator may be provided having a switch configured to be controlled by the CPU 42. Actuation of the motor can cause the source of negative pressure 30 to be activated (e.g., the pump to be turned on), whereas, actuation of the actuator can cause adjustment of the valve(s) 38 to an open state (e.g., rotation of the valve stem to an open state). The switch may be adjusted to an off position by the CPU 42 to turn off the motor, or close the valve(s).

Figure 4:
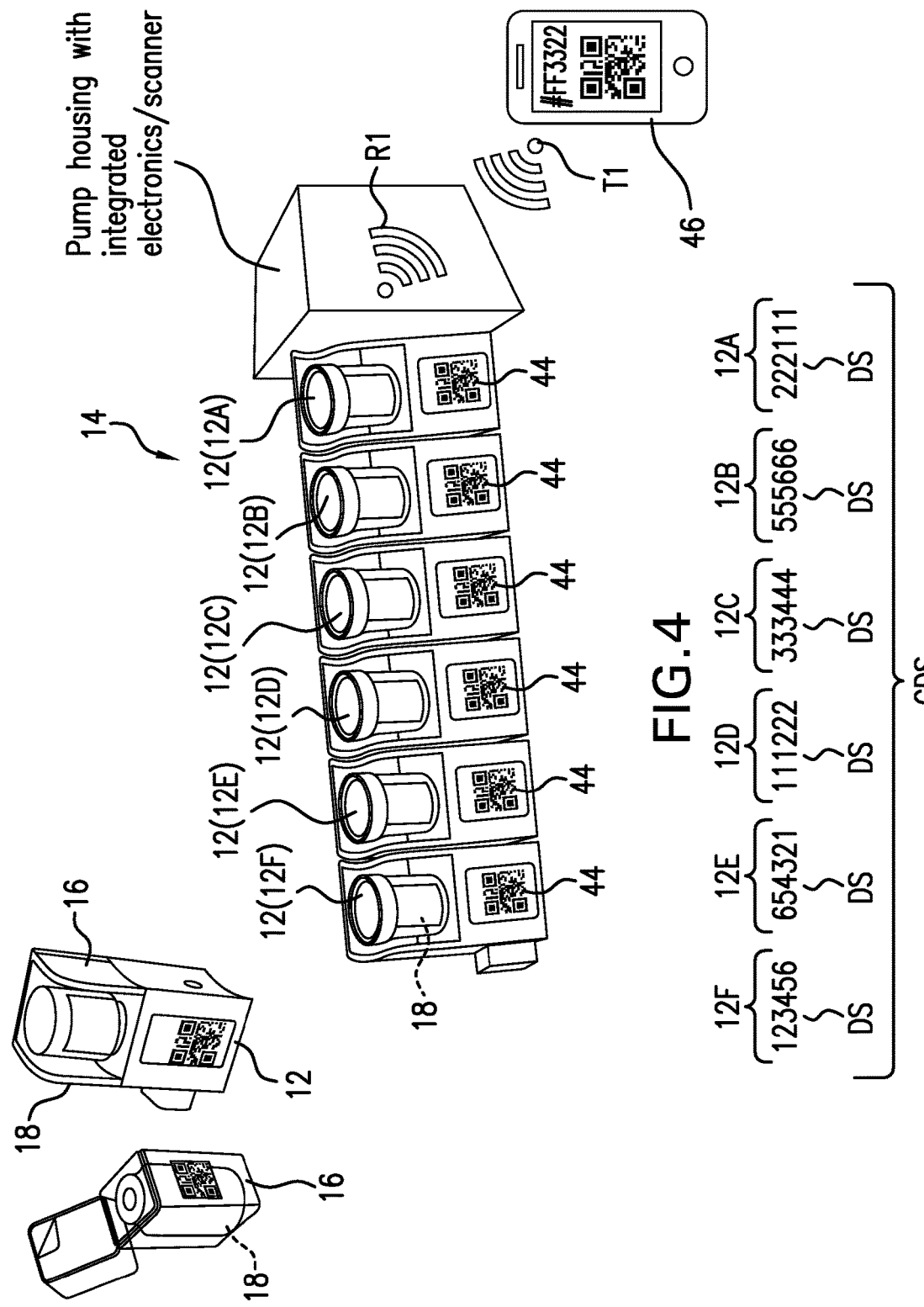
Figure 5:
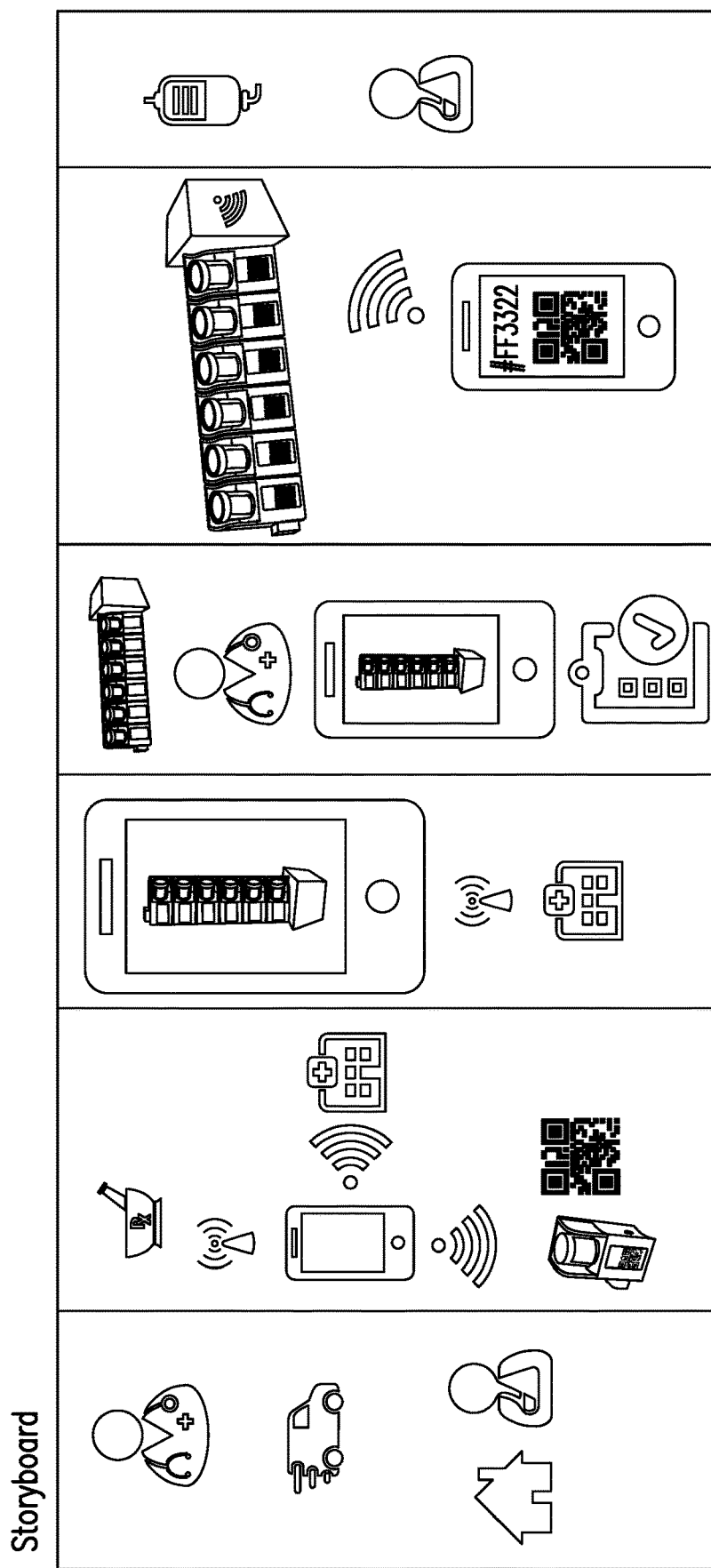

It is envisioned that the drug modules 12 will be serially-connected, when ready for use. Thus, assembly of the drug modules 12 is required by a user, or on behalf of a user. As a fail-safe mechanism, as shown in FIG. 4, to ensure that the drug modules 12 are properly included in the drug delivery device 14 and in the correct sequence, each of the drug modules 12, when loaded with liquid drug 18, may have applied thereto a machine-readable code 44 corresponding to the liquid drug 18. The machine-readable codes 44 are preferably affixed to the drug modules 12 with permanence to avoid the separation of the machine-readable codes 44 from the drug modules 12 during storage or transportation (e.g., stickers with strong adhesive, glue, etching, etc.). The machine-readable codes 44 may be in any format, including bar coding and QR coding. The machine-readable codes 44 are arranged to designate a drug type and, possibly, a drug's concentration or strength. The liquid drug 18 may be loaded into the drug modules 12 in a manufacturing facility or in a pharmacy with the machine-readable codes 44 being affixed at the same time. Care is needed to apply the correct machine-readable codes 44 to the drug modules 12.

The specific liquid drugs 18 (type, concentration) will be specified by prescription. The drug modules 12 will be prepared to accommodate the specified liquid drugs 18—the number of the drug modules 12 to be utilized being at least equal to the number of drug components specified by the prescription. The drug modules 12, along with the controller housing 26, may be delivered to the user or a location associated with the user as a kit, for assembly. Instructions will be provided with regards to the assembly of the drug modules 12, including the sequence of the drug modules 12, e.g., first position (closest to the controller housing 26), second position, and so forth.

Once the drug modules 12 are assembled with the controller housing 26 as the drug delivery device 14, the drug delivery device 14 must be readied to allow for use. To ready the device, a digital image of the entire series of the serially-connected drug modules 12, particularly to include the machine-readable codes 44 of all of the drug modules 12, is captured by a digital camera or a device having a digital camera 46 (smart phone, tablet, notebook, cell phone). The digital image may be captured by the device 46 under the control of a user 45 or through automated means, e.g., where a digital camera is arranged in a facility preparing the drug delivery device 14.

Preferably, the device 46 includes application software 48 configured to read the machine-readable codes 44 to generate an activation code based on the contents of the machine-readable codes 44 and the sequence thereof. For example, the device 46 may be a mobile device, e.g., a smartphone, which includes a digital camera, and on which is accessible the application software 48. Any graphical user interface (GUI) may be provided on the device 46 allowing for interfacing with a user. As appreciated by those skilled in the art, bar code and QR code recognition and reading software is known in the art and is useable with the application software 48. The application software 48 may be stored as a set of instructions on a non-transitory memory associated with the device 46. All or portions of the application software 48 may reside off of the device 46, callable as needed over a network as described below.

Alternatively, the device 46 may be linkable with a secondary device or computer processing unit 47, which may be a remote server, associated with the application software 48. Here, the digital image captured by the device 46 is transmitted to the secondary device or CPU 47 to be read by the application software 48. The device 46 may be linked to the secondary device or CPU 47 via any network 49 (wired, wirelessly, Internet, local area network (LAN), wide area network (WAN)). The secondary device or CPU 47 generates the activation code based on reading the machine-readable codes 44 in the captured image. The secondary device or CPU 47 may be associated with a non-transitory memory 50 on which all or a portion of the application software 48 may be stored as a set of instructions.

As shown in FIG. 4A, the machine-readable codes 44 of each of the drug modules 12 may be used to generate a combined alphanumeric data string CDS, with the individual data strings DS of each of the drug modules 12 being assembled together in the order of the drug modules 12 to produce the activation code.

The activation code may be used for comparison against an authentication code to determine its accuracy. In one embodiment, the authentication code may be stored in a non-transitory memory 41 associated with the CPU 42 in the controller housing 26. The application software 48 may be configured to cause the generated activation code to be transmitted to the CPU 42 (e.g., via a transmitter T1 on the device 46 and a receiver R1 on the controller housing 26) with the CPU 42 running a comparison to determine a match. With a match, the CPU 42 may actuate the flow controller 34 to enable the delivery of the liquid drug 18.

The transmitter T1 and the receiver R1 may be each formed to be a receiver and a transmitter. Any wireless network protocol may be used for wireless communication including, but not limited to, protocols taken from a 802.11-compliant network, Bluetooth network, cellular digital packet data (CDPD) network, high speed circuit switched data (HSCSD) network, packet data cellular (PDC-P) network, general packet radio service (GPRS) network, 1× radio transmission technology (1×RTT) network, IrDA network, multichannel multipoint distribution service (MMDS) network, local multipoint distribution service (LMDS) network, and worldwide interoperability for microwave access (WiMAX) network).

In an alternative embodiment, the application software 48, on the device 46, may be configured to call, e.g., over the network 49, the secondary device or CPU 47 using an application programming interface (API) to retrieve the authentication code therefrom. Alternatively, the device 46 may obtain the authentication code from another source, for example, from a machine-readable code provided with the drug modules 12. Thereafter, the application software 48 may compare, on the device 46, the activation code with the authentication code. With a match, the application software 48 may generate an approval message which is transmitted to the CPU 42, e.g., using the transmitter T1. The expected approval message may be stored in the memory 41. With a match, the CPU 42 may actuate the flow controller 34 to enable the delivery of the liquid drug 18. This embodiment avoids the need for the authentication code to be stored in the controller housing 26.

In a further embodiment, the application software 48, on the device 46, may transmit, e.g., over the network 49, the activation code to the secondary device or CPU 47 for comparison with an authentication code. With a match, the secondary device or CPU 47 transmits, e.g., over the network 49, an approval message to the application software 48, with the application software 48, in turn, transmitting an approval message to the CPU 42, e.g., using the transmitter T1. The expected approval message may be stored in the memory 41. With a match, the CPU 42 may actuate the flow controller 34 to enable the delivery of the liquid drug 18. This embodiment avoids the need for the authentication code to be stored in the controller housing 26.

The flow controller 34 may be provided to have a storage (i.e., non-use) state, e.g., where one or more of the adjustable valves 38 are in closed positions to not permit flow through the delivery tubing 30 to the outlet 32. In addition, or alternatively, in the storage state, the source of negative pressure 36 is in a quiescent state. With a match of the activation code and the authentication code, as described above, the CPU 42 may actuate the flow controller 34, thus causing the flow controller 34 to enter a use state. With the flow controller 34 in a use state, delivery of the liquid drug 18 from the drug delivery device 14 may be achieved. In particular, the one or more adjustable valves 38 may be adjusted to open positions to permit flow through the delivery tubing 30 to the outlet 32. In addition, the source of negative pressure 36 may be actuated, or, alternatively, may be placed into an active state, awaiting actuation (e.g., by a switch on the controller housing 26 and/or through the application software 48 using the device 46).

As will be appreciated by those skilled in the art, the system 10 allows for various functionalities. For example, user accounts may be established, e.g., stored in the memory 50 in the form of a database. Access may be granted to the user accounts by various entities, including a prescribing physician P, a dispensing pharmacy Ph, and/or manufacturing location(s) M which prepare one or more components of the drug delivery device 14. With the user accounts being accessible over the network 49, details of a prescription may be viewed and/or updated as needed. This information may be then used in selecting the liquid drugs 18 to be used in the drug delivery device 14. The user 45 may access his/her account over the network 49 utilizing the device 46, e.g., as mobile device, relying on the GUI to access details as needed.

With the drug delivery device 14 having the receiver R1 configured to also be a transmitter, details (time, date, confirmation of completion) of dosing drug by the drug delivery device 14 may be transmitted over the network 49 to the relevant user accounts. Medical practitioners, such as the prescribing physician P, may access this data to confirm compliance with a dosing regimen.

The system 10 also allows for provision of medical information of a patient useable to determine a prescription. For example, information based on testing of a patient may be uploaded to the user accounts which may be relied upon in determining the prescription. Various physiological parameters and/or biomarkers may be tested with results being uploaded. This would allow for a review from remote locations, such as by the prescribing physician P, with subsequent viewing of the prescription by the pharmacy Ph and/or manufacturing facility M for fulfillment of the prescription. A kit of the prepared drug modules 12 and the controller housing 26 may be forwarded to point-of-use for assembly by the user or an assistant. It is possible that the kit be forwarded to a facility, such as the pharmacy Ph, doctor's office, etc., where the kit is assembled for the patient.

Figure 6:
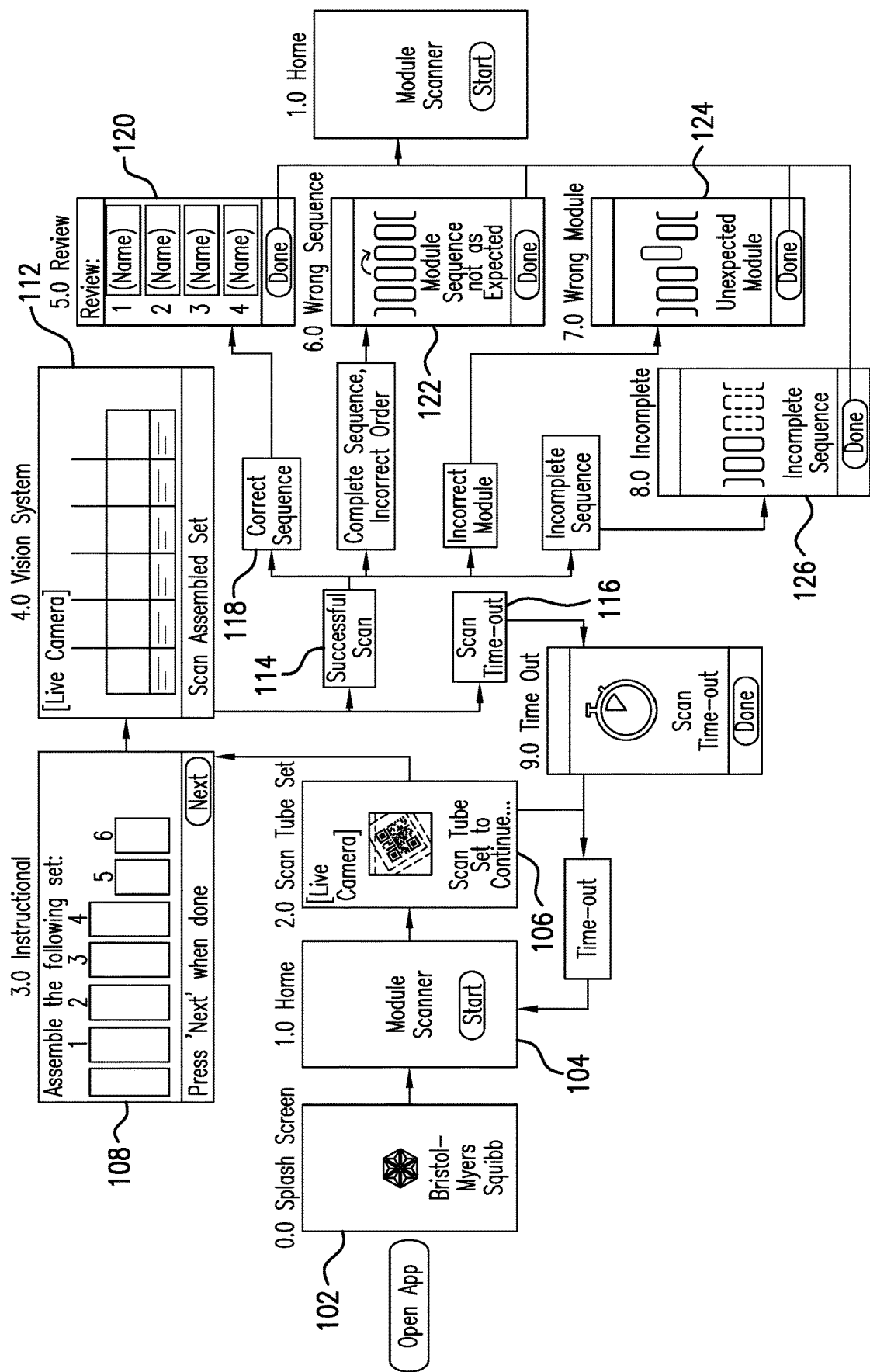
Figure 7:
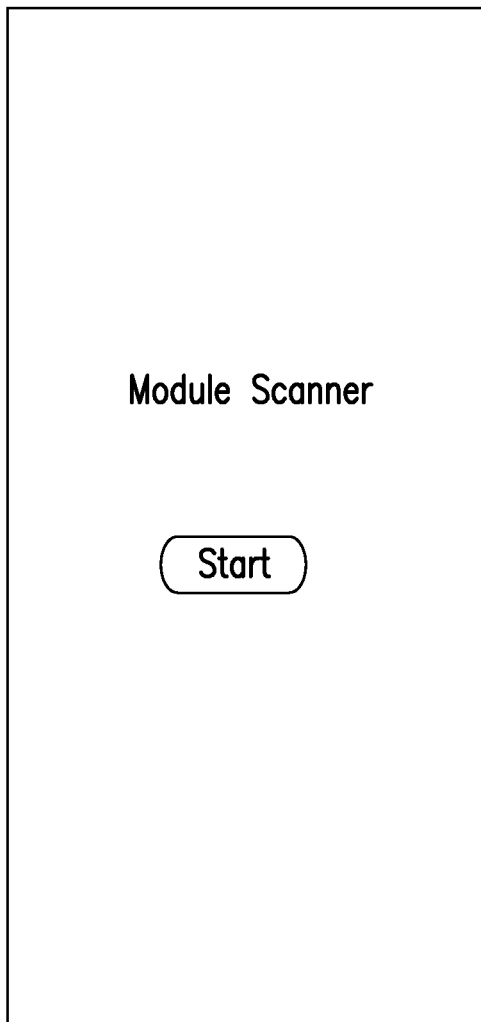
Figure 8:
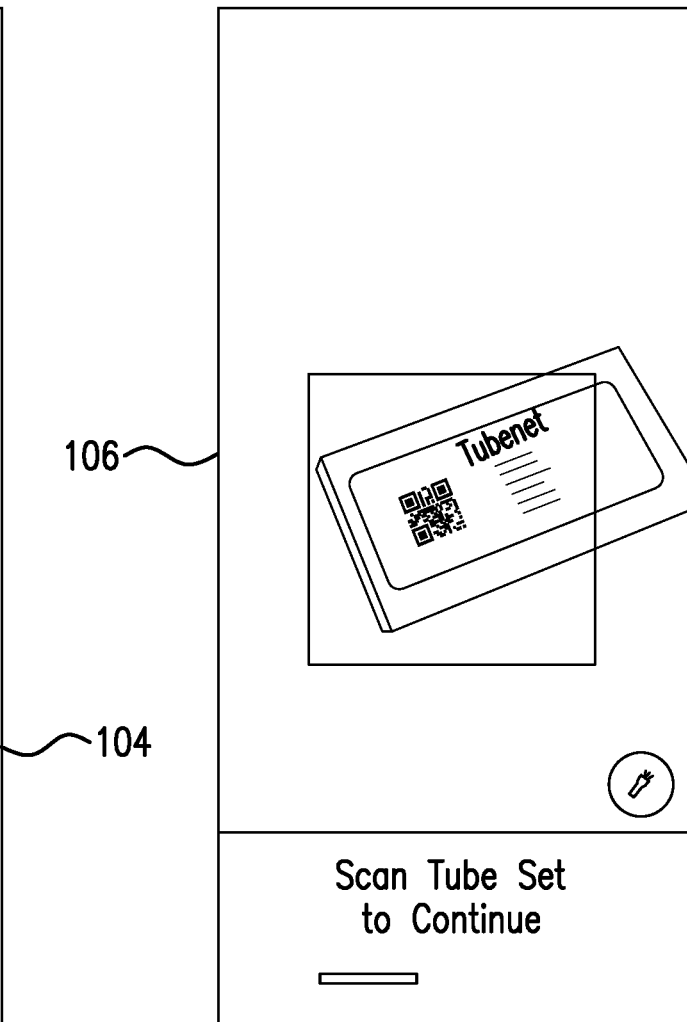
Figure 12:
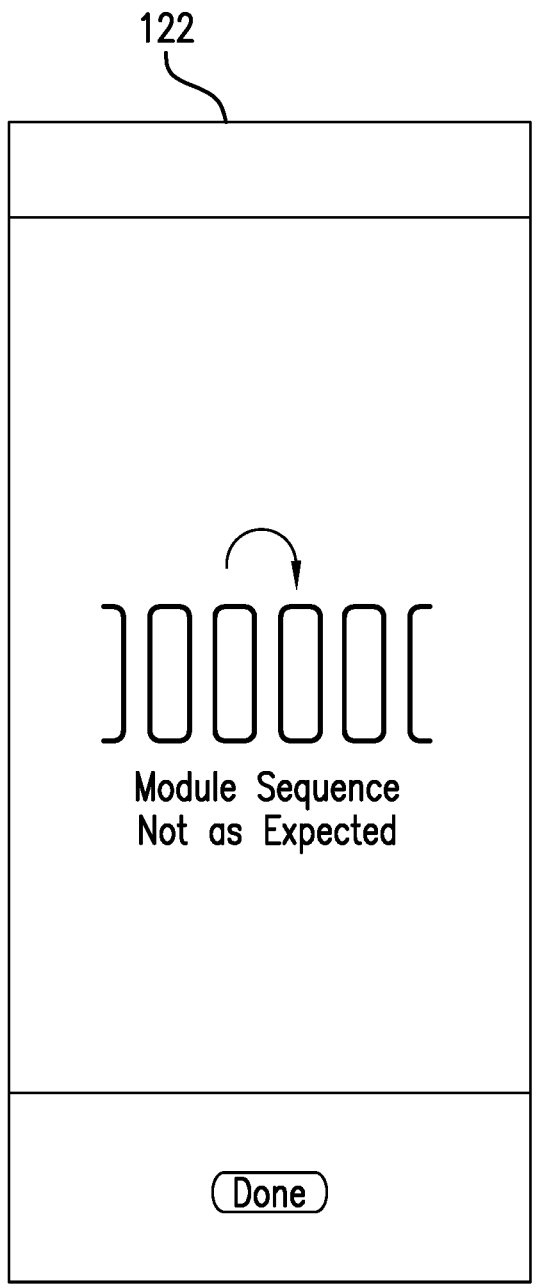
Figure 13:
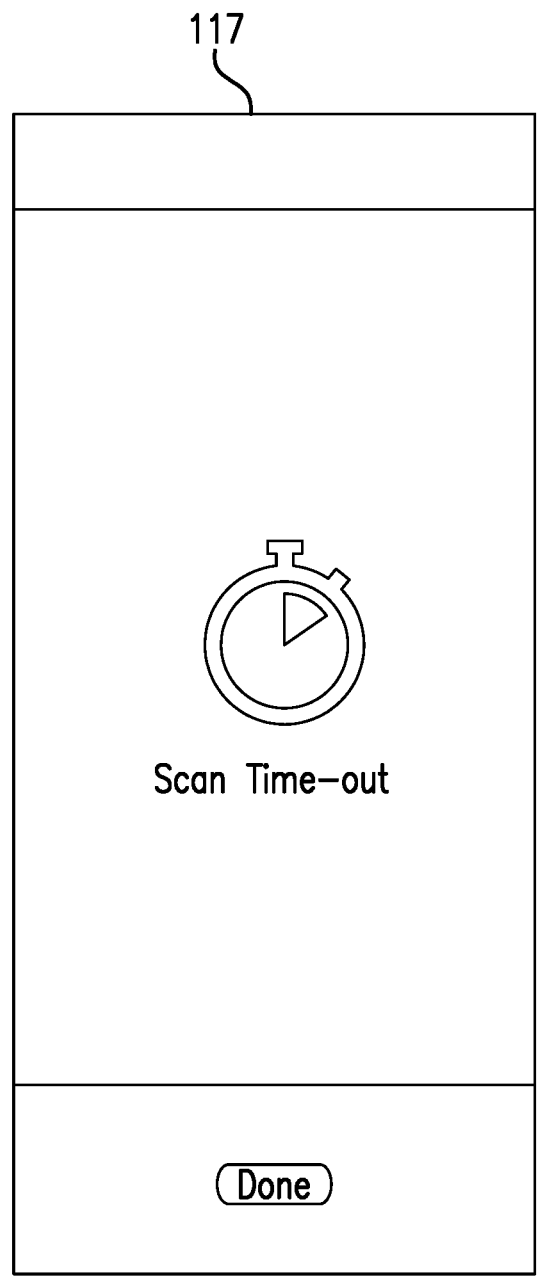
Figure 14:
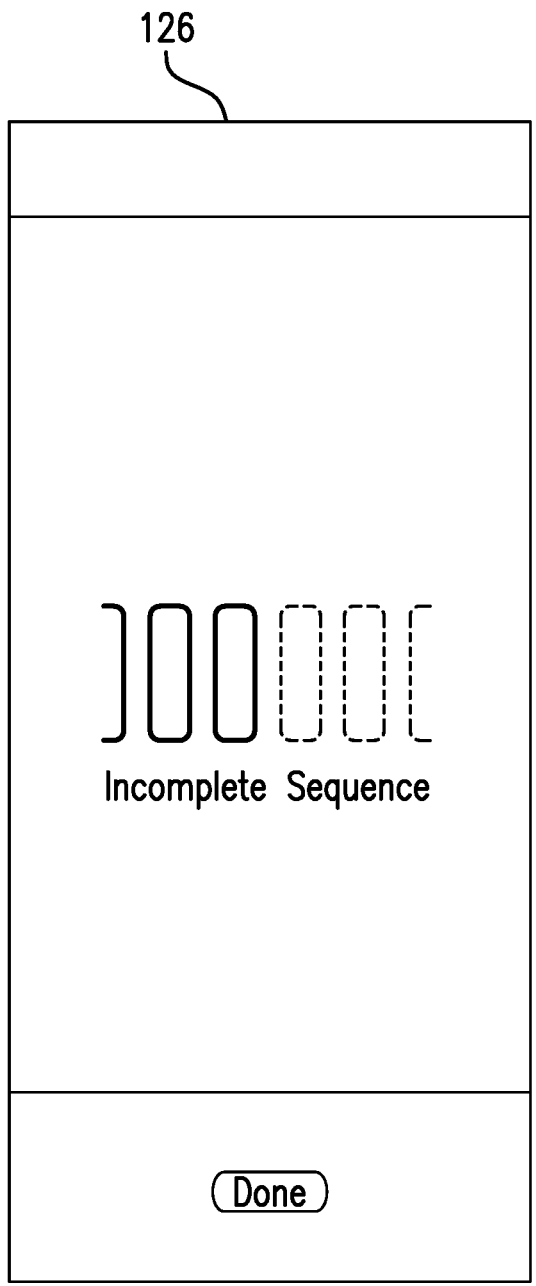
Figure 15:
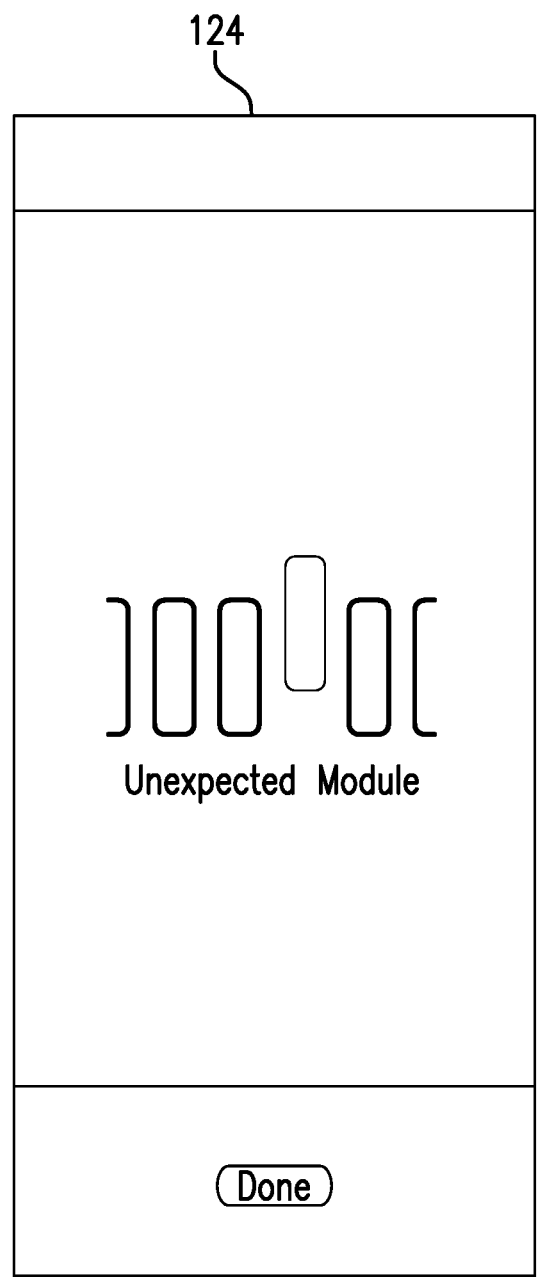

With reference to FIGS. 6-15, a non-limiting example of the process flow of the application software 48 is presented, including GUI's presentable on the device 46 at different stages of the process. With reference to FIG. 6, a useable process flow 100 is depicted starting with a home page or splash screen 102. The process flow 100 continues with a package scanning subroutine having a launch screen 104 and an image reader or capture screen 106 (where a camera on the device 46 may be initiated) to read a machine-readable code on packaging associated with a kit of the drug modules 12, pre-assembly. This subroutine allows for identifying an authentication code associated with a packaged kit of the drug modules 12. This subroutine may time out requiring a return to the launch screen 104 to allow for re-start.

After the package scanning subroutine has been successfully completed, interstitial screen 108 is provided to prompt the user to indicate completion of assembly of the drug modules 12. With the user indicating completion (e.g., by depressing button 110), a drug module scanning subroutine is launched with an image reader or capture screen 112 causing a camera of the device 46 to read or capture all machine-readable codes, in sequence, of the assembled drug modules 12. The application software 48 is configured to generate an activation code based on the machine-readable codes, including the content and sequencing thereof. If the activation code is generated, as indicated in the process flow 100, the scan is considered successful (step 114). If the activation code is not successfully generated, e.g., the scan timed out without proper data capture (as shown by screen 117), the process flow at step 116 returns to the launch screen 104 to repeat the package scanning subroutine.

The application software 48 compares the generated activation code with the obtained authentication code to determine if a match is present. If so, as indicated at step 118, it is determined that the drug modules 12 are proper and in proper sequence. This may launch screen 120 which includes a listing of the drugs, dose amounts, and their sequencing.

If no match is present between the activation code and the authentication code, the basis for lack of match may be determined by the application software 48 and shown as an error. For example, the application software 48 may determine the proper drug modules 12 are present, but in an incorrect sequence, as indicated by error message 122. Alternatively, the application software 48 may determine that one or more of the drug modules 12 is incorrect as indicated by error message 124. Further, the application software 48 may determine that one of more of the drug modules 12 is missing, thus providing an incomplete sequence, as indicated by error message 126. Re-start is possible with return to the launch screen 104.

In one embodiment, any of the combinatorial drug delivery devices disclosed herein is able to deliver two or more drugs for the benefit of the patient suffering from any of a wide range of diseases or conditions, e.g., cancer, autoimmune disorder, inflammatory disorder, cardiovascular disease or fibrotic disorder. In one embodiment, one or more of drug modules 12 may contain a single drug. In one embodiment, one or more of drug module 12 may contain two or more co-formulated drugs. In one embodiment, one or more of drug module 12 may contain a drug in solid form (such as a tablet, capsule, powder, lyophilized, spray dried), which can be reconstituted with flow of a diluent therein to form a liquid drug.

In one embodiment, one or more of the drugs of any of the combinatorial drug delivery devices disclosed herein is an immune checkpoint inhibitor. In certain embodiments, the immune checkpoint inhibitor is Programmed Death-1 ("PD-1") pathway inhibitor, a cytotoxic T-lymphocyte—associated antigen 4 ("CTLA-4") antagonist, a Lymphocyte Activation Gene-3 ("LAG3") antagonist, a CD80 antagonist, a CD86 antagonist, a T cell immunoglobulin and mucin domain ("Tim-3") antagonist, a T cell immunoreceptor with Ig and ITIM domains ("TIGIT") antagonist, a CD20 antagonist, a CD96 antagonist, a Indoleamine 2,3-dioxygenase ("ID01") antagonist, a stimulator of interferon genes ("STING") antagonist, a GARP antagonist, a CD40 antagonist, Adenosine A2A receptor ("A2aR") antagonist, a CEACAM1 (CD66a) antagonist, a CEA antagonist, a CD47 antagonist, a Receptor Related Immunoglobulin Domain Containing Protein ("PVRIG") antagonist, a tryptophan 2,3-dioxygenase ("TDO") antagonist, a V-domain Ig suppressor of T cell activation ("VISTA") antagonist, or a Killer-cell Immunoglobulin-like Receptor ("KIR") antagonist.

In one embodiment, the PD-1 pathway inhibitor is an anti-PD-1 antibody or antigen binding fragment thereof. In certain embodiments, the anti-PD-1 antibody is pembrolizumab (KEYTRUDA; MK-3475), pidilizumab (CT-011), nivolumab (OPDIVO; BMS-936558), PDR001, MEDI0680 (AMP-514), TSR-042, REGN2810, JS001, AMP-224 (GSK-2661380), PF-06801591, BGB-A317, BI 754091, or SHR-1210.

In one embodiment, the PD-1 pathway inhibitor is an anti-PD-L1 antibody or antigen binding fragment thereof. In certain embodiments, the anti-PD-L1 antibody is atezolizumab (TECENTRIQ; RG7446; MPDL3280A; RO5541267), durvalumab (MEDI4736), BMS-936559, avelumab (bavencio), LY3300054, CX-072 (Proclaim-CX-072), FAZ053, KN035, or MDX-1105.

In one embodiment, the PD-1 pathway inhibitor is a small molecule drug. In certain embodiments, the PD-1 pathway inhibitor is CA-170. In another embodiment, the PD-1 pathway inhibitor is a cell based therapy. In one embodiment, the cell based therapy is a MiHA-loaded PD-L1/L2-silenced dendritic cell vaccine. In other embodiments, the cell based therapy is an anti-programmed cell death protein 1 antibody expressing pluripotent killer T lymphocyte, an autologous PD-1-targeted chimeric switch receptor-modified T lymphocyte, or a PD-1 knockout autologous T lymphocyte.

In one embodiment, the PD-1 pathway inhibitor is an anti-PD-L2 antibody or antigen binding fragment thereof. In another embodiment, the anti-PD-L2 antibody is rHIgM12B7.

In one embodiment, the PD-1 pathway inhibitor is a soluble PD-1 polypeptide. In certain embodiments, the soluble PD-1 polypeptide is a fusion polypeptide. In some embodiments, the soluble PD-1 polypeptide comprises a ligand binding fragment of the PD-1 extracellular domain. In other embodiments, the soluble PD-1 polypeptide comprises a ligand binding fragment of the PD-1 extracellular domain. In another embodiment, the soluble PD-1 polypeptide further comprises an Fc domain.

In one embodiment, the immune checkpoint inhibitor is a CTLA-4 antagonist. In certain embodiments, the CTLA-4 antagonist is an anti-CTLA-4 antibody or antigen binding fragment thereof. In some embodiments, the anti-CTLA-4 antibody is ipilimumab (YERVOY), tremelimumab (ticilimumab; CP-675,206), AGEN-1884, or ATOR-1015. In one embodiment, any of the combinatorial drug delivery devices disclosed herein includes a CTLA-4 antagonist, e.g., ipilimumab (YERVOY), and a PD-1 pathway inhibitor, e.g., nivolumab (OPDIVO) or pembrolizumab (KEYTRUDA).

In one embodiment, the immune checkpoint inhibitor is an antagonist of LAG3. In certain embodiments, the LAG3 antagonist is an anti-LAG3 antibody or antigen binding fragment thereof. In certain embodiments, the anti-LAG3 antibody is relatlimab (BMS-986016), MK-4280 (28G-10), REGN3767, GSK2831781, IMP731 (H5L7BW), BAP050, IMP-701 (LAG-5250), IMP321, TSR-033, LAG525, BI 754111, or FS-118. In one embodiment, any of the combinatorial drug delivery devices disclosed herein includes a LAG3 antagonist, e.g., relatlimab or MK-4280, and a PD-1 pathway inhibitor, e.g., nivolumab (OPDIVO) or pembrolizumab (KEYTRUDA). In one embodiment, any of the combinatorial drug delivery devices disclosed herein includes a LAG3 antagonist, e.g., relatlimab or MK-4280, and a CTLA-4 antagonist, e.g., ipilimumab (YERVOY). In one embodiment, any of the combinatorial drug delivery devices disclosed herein includes a LAG3 antagonist, e.g., relatlimab or MK-4280, a CTLA-4 antagonist, e.g., ipilimumab (YERVOY), and a PD-1 pathway inhibitor, e.g., nivolumab (OPDIVO) or pembrolizumab (KEYTRUDA).

In one embodiment, the immune checkpoint inhibitor is a KIR antagonist. In certain embodiments, the KIR antagonist is an anti-KIR antibody or antigen binding fragment thereof. In some embodiments, the anti-KIR antibody is lirilumab (1-7F9, BMS-986015, IPH 2101) or IPH4102.

In one embodiment, the immune checkpoint inhibitor is TIGIT antagonist. In one embodiment, the TIGIT antagonist is an anti-TIGIT antibody or antigen binding fragment thereof. In certain embodiments, the anti-TIGIT antibody is BMS-986207, AB 154, COM902 (CGEN-15137), or OMP-313M32.

In one embodiment, the immune checkpoint inhibitor is Tim-3 antagonist. In certain embodiments, the Tim-3 antagonist is an anti-Tim-3 antibody or antigen binding fragment thereof. In some embodiments, the anti-Tim-3 antibody is TSR-022 or LY3321367.

In one embodiment, the immune checkpoint inhibitor is an IDOL antagonist. In another embodiment, the IDOL antagonist is indoximod (NLG8189; 1-methyl-D-TRP), epacadostat (INCB-024360, INCB-24360), KHK2455, PF-06840003, navoximod (RG6078, GDC-0919, NLG919), BMS-986205 (F001287), or pyrrolidine-2,5-dione derivatives.

In one embodiment, the immune checkpoint inhibitor is a STING antagonist. In certain embodiments, the STING antagonist is 2' or 3'-mono-fluoro substituted cyclic-di-nucleotides; 2'3'-di-fluoro substituted mixed linkage 2', 5'-3', 5' cyclic-di-nucleotides; 2'-fluoro substituted, bis-3', 5' cyclic-di-nucleotides; 2', 2''-diF-Rp,Rp,bis-3', 5' cyclic-di-nucleotides; or fluorinated cyclic-di-nucleotides.

In one embodiment, the immune checkpoint inhibitor is CD20 antagonist. In some embodiments, the CD20 antagonist is an anti-CD20 antibody or antigen binding fragment thereof. In one embodiment, the anti-CD20 antibody is rituximab (RITUXAN; IDEC-102; IDEC-C2B8), ABP 798, ofatumumab, or obinutuzumab.

In one embodiment, the immune checkpoint inhibitor is CD80 antagonist. In certain embodiments, the CD80 antagonist is an anti-CD80 antibody or antigen binding fragment thereof. In one embodiment, the anti-CD80 antibody is galiximab or AV 1142742.

In one embodiment, the immune checkpoint inhibitor is a GARP antagonist. In some embodiments, the GARP antagonist is an anti-GARP antibody or antigen binding fragment thereof. In certain embodiments, the anti-GARP antibody is ARGX-115.

In one embodiment, the immune checkpoint inhibitor is a CD40 antagonist. In certain embodiments, the CD40 antagonist is an anti-CD40 antibody for antigen binding fragment thereof. In some embodiments, the anti-CD40 antibody is BMS3h-56, lucatumumab (HCD122 and CHIR-12.12), CHIR-5.9, or dacetuzumab (huS2C6, PRO 64553, RG 3636, SGN 14, SGN-40). In another embodiment, the CD40 antagonist is a soluble CD40 ligand (CD40-L). In one embodiment, the soluble CD40 ligand is a fusion polypeptide. In one embodiment, the soluble CD40 ligand is a CD40-L/FC2 or a monomeric CD40-L.

In one embodiment, the immune checkpoint inhibitor is an A2aR antagonist. In some embodiments, the A2aR antagonist is a small molecule. In certain embodiments, the A2aR antagonist is CPI-444, PBF-509, istradefylline (KW-6002), preladenant (SCH420814), tozadenant (SYN115), vipadenant (BIIB014), HTL-1071, ST1535, SCH412348, SCH442416, SCH58261, ZM241385, or AZD4635.

In one embodiment, the immune checkpoint inhibitor is a CEACAM1 antagonist. In some embodiments, the CEACAM1 antagonist is an anti-CEACAM1 antibody or antigen binding fragment thereof. In one embodiment, the anti-CEACAM1 antibody is CM-24 (MK-6018).

In one embodiment, the immune checkpoint inhibitor is a CEA antagonist. In one embodiment, the CEA antagonist is an anti-CEA antibody or antigen binding fragment thereof. In certain embodiments, the anti-CEA antibody is cergutuzumab amunaleukin (RG7813, RO-6895882) or RG7802 (RO6958688).

In one embodiment, the immune checkpoint inhibitor is a CD47 antagonist. In some embodiments, the CD47 antagonist is an anti-CD47 antibody or antigen binding fragment thereof. In certain embodiments, the anti-CD47 antibody is HuF9-G4, CC-90002, TTI-621, ALX148, NI-1701, NI-1801, SRF231, or Effi-DEM.

In one embodiment, the immune checkpoint inhibitor is a PVRIG antagonist. In certain embodiments, the PVRIG antagonist is an anti-PVRIG antibody or antigen binding fragment thereof. In one embodiment, the anti-PVRIG antibody is COM701 (CGEN-15029).

In one embodiment, the immune checkpoint inhibitor is a TDO antagonist. In one embodiment, the TDO antagonist is a 4-(indol-3-yl)-pyrazole derivative, a 3-indol substituted derivative, or a 3-(indol-3-yl)-pyridine derivative. In another embodiment, the immune checkpoint inhibitor is a dual IDO and TDO antagonist. In one embodiment, the dual IDO and TDO antagonist is a small molecule.

In one embodiment, the immune checkpoint inhibitor is a VISTA antagonist. In some embodiments, the VISTA antagonist is CA-170 or JNJ-61610588.

In one embodiment, one or more of the drugs of any of the combinatorial drug delivery devices disclosed herein is an immune checkpoint enhancer or stimulator.

In one embodiment, the immune checkpoint enhancer or stimulator is a CD28 agonist, a 4-1BB agonist, an OX40 agonist, a CD27 agonist, a CD80 agonist, a CD86 agonist, a CD40 agonist, an ICOS agonist, a CD70 agonist, or a GITR agonist.

In one embodiment, the immune checkpoint enhancer or stimulator is an OX40 agonist. In certain embodiments, the OX40 agonist is an anti-OX40 antibody or antigen binding fragment thereof. In some embodiments, the anti-OX40 antibody is tavolixizumab (MEDI-0562), pogalizumab (MOXR0916, RG7888), GSK3174998, ATOR-1015, MEDI-6383, MEDI-6469, BMS 986178, PF-04518600, or RG7888 (MOXR0916). In another embodiment, the OX40 agonist is a cell based therapy. In certain embodiments, the OX40 agonist is a GINAKIT cell (iC9-GD2-CD28-OX40-expressing T lymphocytes).

In one embodiment, the immune checkpoint enhancer or stimulator is a CD40 agonist. In some embodiments, the CD40 agonist is an anti-CD40 antibody or antigen binding fragment thereof. In one embodiment, the anti-CD40 antibody is ADC-1013 (JNJ-64457107), RG7876 (RO-7009789), HuCD40-M2, APX005M (EPI-0050), or Chi Lob 7/4. In another embodiment, the CD40 agonist is a soluble CD40 ligand (CD40-L). In one embodiment, the soluble CD40 ligand is a fusion polypeptide. In certain embodiments, the soluble CD40 ligand is a trimeric CD40-L (AVREND®).

In one embodiment, the immune checkpoint enhancer or stimulator is a GITR agonist. In certain embodiments, the GITR agonist is an anti-GITR antibody or antigen binding fragment thereof. In one embodiment, the anti-GITR antibody is BMS-986156, TRX518, GWN323, INCAGN01876, or MEDI1873. In one embodiment, the GITR agonist is a soluble GITR ligand (GITRL). In some embodiments, the soluble GITR ligand is a fusion polypeptide. In another embodiment, the GITR agonist is a cell based therapy. In one embodiment, the cell based therapy is an anti-CTLA4 mAb RNA/GITRL RNA-transfected autologous dendritic cell vaccine or a GITRL RNA-transfected autologous dendritic cell vaccine.

In one embodiment, the immune checkpoint enhancer or stimulator a 4-1BB agonist. In some embodiments, the 4-1BB agonist is an anti-4-1BB antibody or antigen binding fragment thereof. In one embodiment, the anti-4-1BB antibody is urelumab or PF-05082566.

In one embodiment, the immune checkpoint enhancer or stimulator is a CD80 agonist or a CD86 agonist. In some embodiments, the CD80 agonist or the CD86 agonist is a soluble CD80 or CD86 ligand (CTLA-4). In certain embodiments, the soluble CD80 or CD86 ligand is a fusion polypeptide. In one embodiment, the CD80 or CD86 ligand is CTLA4-Ig (CTLA4-IgG4m, RG2077, or RG1046) or abatacept (ORENCIA, BMS-188667). In other embodiments, the CD80 agonist or the CD86 agonist is a cell based therapy. In one embodiment, the cell based therapy is MGN1601 (an allogeneic renal cell carcinoma vaccine).

In one embodiment, the immune checkpoint enhancer or stimulator is a CD28 agonist. In some embodiments, the CD28 agonist is an anti-CD28 antibody or antigen binding fragment thereof. In certain embodiments, the anti-CD28 antibody is TGN1412.

In one embodiment, the CD28 agonist is a cell based therapy. In certain embodiments, the cell based therapy is JCAR015 (anti-CD19-CD28-zeta modified CAR CD3+T lymphocyte); CD28CAR/CD137CAR-expressing T lymphocyte; allogeneic CD4+ memory Th1-like T cells/microparticle-bound anti-CD3/anti-CD28; anti-CD19/CD28/CD3 zeta CAR gammaretroviral vector-transduced autologous T lymphocytes KTE-C19; anti-CEA IgCD28TCR-transduced autologous T lymphocytes; anti-EGFRvIII CAR-transduced allogeneic T lymphocytes; autologous CD123CAR-CD28-CD3zeta-EGFRt-expressing T lymphocytes; autologous CD171-specific CAR-CD28 zeta-4-1-BB-EGFRt-expressing T lymphocytes; autologous CD19CAR-CD28-CD3zeta-EGFRt-expressing Tcm-enriched T cells; autologous PD-1-targeted chimeric switch receptor-modified T lymphocytes (chimera with CD28); CD19CAR-CD28-CD3zeta-EGFRt-expressing Tcm-enriched T lymphocytes; CD19CAR-CD28-CD3zeta-EGFRt-expressing Tn/mem-enriched T lymphocytes; CD19CAR-CD28zeta-4-1BB-expressing allogeneic T lymphocytes; CD19CAR-CD3zeta-4-1BB-CD28-expressing autologous T lymphocytes; CD28CAR/CD137CAR-expressing T lymphocytes; CD3/CD28 costimulated vaccine-primed autologous T lymphocytes; or iC9-GD2-CD28-OX40-expressing T lymphocytes.

In one embodiment, the immune checkpoint enhancer or stimulator is a CD27 agonist. In certain embodiments, the CD27 agonist is an anti-CD27 antibody or antigen binding fragment thereof. In one embodiment, the anti-CD27 antibody is varlilumab (CDX-1127).

In one embodiment, the immune checkpoint enhancer or stimulator is a CD70 agonist. In some embodiments, the CD70 agonist is an anti-CD70 antibody or antigen binding fragment thereof. In one embodiment, the anti-CD70 antibody is ARGX-110.

In one embodiment, the immune checkpoint enhancer or stimulator is an ICOS agonist. In certain embodiments, the ICOS agonist is an anti-ICOS antibody or antigen binding fragment thereof. In some embodiments, the anti-ICOS antibody is BMS986226, MEDI-570, GSK3359609, or JTX-2011. In other embodiments, the ICOS agonist is a soluble ICOS ligand. In some embodiments, the soluble ICOS ligand is a fusion polypeptide. In one embodiment, the soluble ICOS ligand is AMG 750.

In one embodiment, one or more of the drugs of any of the combinatorial drug delivery devices disclosed herein is an anti-CD73 antibody or antigen binding fragment thereof. In certain embodiments, the anti-CD73 antibody is MEDI9447.

In one embodiment, one or more of the drugs of any of the combinatorial drug delivery devices disclosed herein is a TLR9 agonist. In one embodiment, the TLR9 agonist is agatolimod sodium.

In one embodiment, one or more of the drugs of any of the combinatorial drug delivery devices disclosed herein is a cytokine. In certain embodiments, the cytokine is a chemokine, an interferon, an interleukin, lymphokine, or a member of the tumor necrosis factor family. In some embodiments, the cytokine is IL-2, IL-15, or interferon-gamma.

In one embodiment, one or more of the drugs of any of the combinatorial drug delivery devices disclosed herein is a TGF-β antagonist. In some embodiments, the TGF-β antagonist is fresolimumab (GC-1008); NIS793; IMC-TR1 (LY3022859); ISTH0036; trabedersen (AP 12009); recombinant transforming growth factor-beta-2; autologous HPV-16/18 E6/E7-specific TGF-beta-resistant T lymphocytes; or TGF-beta-resistant LMP-specific cytotoxic T-lymphocytes.

In one embodiment, one or more of the drugs of any of the combinatorial drug delivery devices disclosed herein is an iNOS antagonist. In some embodiments, the iNOS antagonist is N-Acetyle-cysteine (NAC), aminoguanidine, L-nitroarginine methyl ester, or S,S-1,4-phenylene-bis(1,2-ethanediyl)bis-isothiourea).

In one embodiment, one or more of the drugs of any of the combinatorial drug delivery devices disclosed herein is a SHP-1 antagonist.

In one embodiment, one or more of the drugs of any of the combinatorial drug delivery devices disclosed herein is a colony stimulating factor 1 receptor ("CSF1R") antagonist. In certain embodiments, the CSF1R antagonist is an anti-CSF1R antibody or antigen binding fragment thereof. In some embodiments, the anti-CSF1R antibody is emactuzumab.

In one embodiment, one or more of the drugs of any of the combinatorial drug delivery devices disclosed herein is an agonist of a TNF family member. In some embodiments, the agonist of the TNF family member is ATOR 1016, ABBV-621, or Adalimumab.

In one embodiment, one or more of the drugs of any of the combinatorial drug delivery devices disclosed herein is an Interleukin-2 (IL-2), such as aldesleukin. Preferably, the IL-2 or conjugated IL-2 (e.g., pegylated) has been modified to selectively activate T-effector cells over T-regulatory cells ("T-eff IL-2"), such as bempegaldesleukin. In one embodiment, any of the combinatorial drug delivery devices disclosed herein includes a modified IL-2, such as bempegaldesleukin, which selectively activates T-effector cells over T-regulatory cells, and a PD-1 pathway inhibitor, e.g., nivolumab (OPDIVO) or pembrolizumab (KEYTRUDA). In one embodiment, any of the combinatorial drug delivery devices disclosed herein includes a modified IL-2, such as bempegaldesleukin, which selectively activates T-effector cells over T-regulatory cells, and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells, and a PD-1 pathway inhibitor, e.g., nivolumab (OPDIVO) or pembrolizumab (KEYTRUDA), and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells and a CTLA-4 antagonist, e.g., ipilimumab (YERVOY). In one embodiment, any of the combinatorial drug delivery devices disclosed herein includes a modified IL-2, such as bempegaldesleukin, which selectively activates T-effector cells over T-regulatory cells, a PD-1 pathway inhibitor, e.g., nivolumab (OPDIVO) or pembrolizumab (KEYTRUDA), and a CTLA-4 antagonist, e.g., ipilimumab (YERVOY). In one embodiment, any of the combinatorial drug delivery devices disclosed herein includes a modified IL-2, such as bempegaldesleukin, which selectively activates T-effector cells over T-regulatory cells, a CTLA-4 antagonist, e.g., ipilimumab (YERVOY), and a LAG3 antagonist, e.g., relatlimab or MK-4280. In one embodiment, any of the combinatorial drug delivery devices disclosed herein includes a modified IL-2, such as bempegaldesleukin, which selectively activates T-effector cells over T-regulatory cells, a PD-1 pathway inhibitor, e.g., nivolumab (OPDIVO) or pembrolizumab (KEYTRUDA), a CTLA-4 antagonist, e.g., ipilimumab (YERVOY), and a LAG3 antagonist, e.g., relatlimab or MK-4280.

In one embodiment, one or more of the drugs of any of the combinatorial drug delivery devices disclosed herein is a CD160 (NK1) agonist. In certain embodiments, the CD160 (NK1) agonist is an anti-CD160 antibody or antigen binding fragment thereof. In one embodiment, the anti-CD160 antibody is BY55.

In one embodiment, the one or more of drug module 12 may contain a soluble CTLA-4 polypeptide, which can be useful for treating, for instance, T-cell mediated autoimmune disorders, such as rheumatoid arthritis, juvenile idiopathic arthritis, psoriatic arthritis, graft-versus-host disease, and transplant rejection. In one embodiment, the soluble CTLA-4 polypeptide is abatacept (ORENCIA), belatacept (NULOJIX), RG2077, or RG-1046. In certain embodiments, one or more drug modules 12 of a combinatorial drug delivery device as described herein include a soluble CTLA-4 polypeptide, e.g., abatacept (ORENCIA) and a Bruton's tyrosine kinase inhibitor, e.g., branebrutinib. In certain embodiments, one or more drug modules 12 of a combinatorial drug delivery device as described herein include a soluble CTLA-4 polypeptide, e.g., abatacept (ORENCIA) and a tyrosine kinase-2 inhibitor, e.g., BMS-986165. In certain embodiments, one or more drug modules 12 of a combinatorial drug delivery device as described herein include a soluble CTLA-4 polypeptide, e.g., abatacept (ORENCIA) and an Interleukin-2 (IL-2) or "T-reg IL-2", which selectively activates T-regulatory cells as opposed to T-effector cells, e.g., BMS-986326 and NKTR-358.

What is claimed is:

1. A method of preparing a combinatorial drug delivery device for a patient, the method comprising:
preparing a plurality of serially-connectable drug modules, each containing a drug component or diluent, for the patient;
affixing a machine-readable code to each of the plurality of drug modules, wherein the machine-readable codes each represent an alphanumeric data string associated with the drug component or diluent contained in the corresponding drug module; and,
associating an authentication code with the plurality of drug modules, wherein the authentication code is based on a combination of the alphanumeric data strings assembled together in a pre-defined sequence of the plurality of drug modules being serially connected.

2. The method of claim 1, further comprising: providing a flow controller.

3. The method of claim 2, further comprising: providing a control unit having a computing processing unit configured to actuate the flow controller.

4. The method of claim 3, further comprising storing the authentication code on a non-transitory memory associated with the computing processing unit.

5. The method of claim 4, wherein the computing processing unit is configured to actuate the flow controller based on a match between the authentication code and an activation code received by the computing processing unit.

6. The method of claim 3, wherein the computing processing unit is configured to actuate the flow controller based on an approval message received by the computing processing unit, the approval message being generated remotely from the computing processing unit based on the authentication code.

7. The method of claim 3, wherein the flow controller and the control unit are contained in a controller housing.

8. The method of claim 7, further comprising: delivering the plurality of drug modules and the controller housing to a point of assembly.

9. The method of claim 1, wherein the machine-readable codes are selected from one or more of the group consisting of: QR codes and bar codes.

10. The method of claim 1, wherein each of the machine-readable codes represents a type of the drug component or diluent contained in the corresponding drug module.

11. The method of claim 10, wherein each of the machine-readable codes represents a concentration of the drug component contained in the corresponding drug module.

12. The method of claim 1, wherein the plurality of drug modules is prepared for the patient based on a prescription for the patient.

13. A method of preparing a combinatorial drug delivery device for a patient, the method comprising:
preparing a plurality of drug modules, each containing a drug component or diluent, for the patient;
affixing a machine-readable code to each of the plurality of drug modules, wherein the machine-readable codes each represent an alphanumeric data string associated with the drug component or diluent contained in the corresponding drug module;
associating an authentication code with the plurality of drug modules, wherein the authentication code is based on a combination of the alphanumeric data strings assembled together in a sequence of the plurality of drug modules pre-defined for the patient;
providing a flow controller;
providing a control unit having a computing processing unit configured to actuate the flow controller; and,
storing the authentication code on a non-transitory memory associated with the computing processing unit, wherein the computing processing unit is configured to actuate the flow controller based on a match between the authentication code and an activation code received by the computing processing unit.

14. The method of claim 13, wherein the flow controller and the control unit are contained in a controller housing.

15. The method of claim 14, further comprising: delivering the plurality of drug modules and the controller housing to a point of assembly.

16. The method of claim 13, wherein the machine-readable codes are selected from one or more of the group consisting of: QR codes and bar codes.

17. The method of claim 13, wherein each of the machine-readable codes represents a type of the drug component or diluent contained in the corresponding drug module.

18. The method of claim 13, wherein each of the machine-readable codes represents a concentration of the drug component contained in the corresponding drug module.

19. The method of claim 13, wherein the plurality of drug modules is prepared for the patient based on a prescription for the patient.

* * * * *